United States Patent [19]

Turnbull et al.

[11] Patent Number: 4,547,518
[45] Date of Patent: Oct. 15, 1985

[54] ANTIEMETIC N-(1-SUBSTITUTED-4,5-DIHYDRO-1H-PYRAZOL-4-YL)BENZAMIDES

[75] Inventors: Lennox B. Turnbull; John A. Donohue; Gunnar E. Jagdmann, Jr., all of Richmond, Va.

[73] Assignee: A. H. Robins Company, Incorporated, Richmond, Va.

[21] Appl. No.: 597,421

[22] Filed: Apr. 6, 1984

[51] Int. Cl.$^4$ .................. A61K 31/415; C07D 231/06
[52] U.S. Cl. ........................ 514/403; 548/379
[58] Field of Search ................ 548/358, 379; 424/273 P

[56] References Cited

U.S. PATENT DOCUMENTS

| | | | |
|---|---|---|---|
| 3,236,858 | 2/1966 | Peterli et al. | 548/379 |
| 3,995,044 | 11/1976 | Kabbe et al. | 548/379 |
| 4,207,327 | 6/1980 | Lunsford et al. | 424/273 P |

OTHER PUBLICATIONS

Knorr et al., *Ber.*, 26, p. 104, (1893).

*Primary Examiner*—Richard A. Schwartz
*Assistant Examiner*—Kurt G. Briscoe

[57] ABSTRACT

N-(1-Substituted-4,5-dihydro-1H-pyrazol-4-yl)benzamides having the general formula:

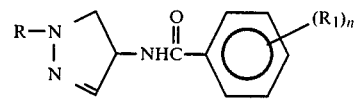

wherein R is loweralkyl, cycloalkyl or phenylloweralkyl and $R_1$ is selected from hydroxy, cyano, nitro, amino, methylamino, dimethylamino, halo, trifluoromethyl, loweralkyl, loweralkoxy, sulfamoyl or acetamido, and when n is more than 1 up to 3, $R_1$ can be the same or different, are disclosed as having gastrokinetic and anti-emetic utility in animals and pharmaceutical compositions therefor. A process for preparing the compounds by oxidation of 1,2-disubstituted-N-(4-pyrazolidinyl)benzamides with a metal hypochlorite is disclosed.

10 Claims, No Drawings

ANTIEMETIC N-(1-SUBSTITUTED-4,5-DIHYDRO-1H-PYRAZOL-4-YL)BENZAMIDES

BACKGROUND OF THE INVENTION

1. Field of the Invention

The present invention relates to certain novel N-(1-substituted-4,5-dihydro-1H-pyrazol-4-yl)benzamides and methods and novel process of preparation, pharmaceutical methods and compositions associated therewith. The compounds have gastrokinetic and antiemetic activity in warm blooded animals.

2. Information Disclosure Statement

A search of the prior art did not reveal the N-(1-substituted-4,5-dihydro-1H-pyrazol-4-yl)benzamides of the present invention (Formula I).

The materials used to prepare the compounds of this invention are the N-(1,2-disubstituted-4-pyrazolidinyl)benzamides such as are described in U.S. Pat. No. 4,207,327.

One of the compounds of the present invention; namely, 4-amino-5-chloro-N-(1-ethyl-4,5-dihydro-1H-pyrazol-4-yl)-2-methoxybenzamide, was discovered as a metabolite in the blood stream and excrement of animals treated with 4-amino-5-chloro-N-(1,2-diethyl-4-pyrazolidinyl)-2-methoxybenzamide.

SUMMARY OF THE INVENTION

The N-(1-substituted-4,5-dihydro-1H-pyrazol-4-yl)benzamide compounds of the present invention have the formula:

Formula I wherein;

R is selected from loweralkyl, cycloalkyl, or phenyloweralkyl;

$R_1$ is selected from hydroxy, cyano, nitro, amino, methylamino, dimethylamino, halo, trifluoromethyl, loweralkyl, loweralkoxy, sulfamoyl or acetamido;

n is an integer from 1 to 3 inclusive, and $R_1$ can be the same radical or different radicals.

In the further definition of symbols in the formulas hereof and where they appear elsewhere throughout this specification and the claims, the terms have the following significance.

The term "loweralkyl" as used herein includes straight and branched chain radicals of up to eight carbons inclusive and is exemplified by such groups as methyl, ethyl, propyl, isopropyl, butyl, amyl, hexyl, heptyl and octyl radicals and the like. The term "loweralkoxy" has the formula —O—loweralkyl.

The terms "halo" and "halogen" when referred to herein include fluorine, chlorine, bromine and iodine unless otherwise stated.

Protected amino groups used in synthesis are acetylamino or benzoylamino radicals and the like on the benzamide moiety mentioned hereinbelow in synthetic methods.

The gastric emptying activity was determined by the method of Droppleman, D., Gregory, R, and Alphin, R., J. Pharmacological Methods 4 (3) 227–30 (1980) wherein the rate of emptying of a test meal in 10 rats compared to controls was observed. Indicative of the activity of a preferred compound of Example 1 is the result obtained by intraperitoneal administration of 10.0 mg/kg which significantly increased gastric emptying by 42% (as determined by the Student t-test) 60 minutes after feeding the test meal.

Anti-emetic properties are exhibited in the compounds when tested by the procedure of Chen and Enxor. J. Pharmac. Exp. Ther. 98, 245–250 (1950) and Leonard, A. et al., J. Pharmac. Exp. Ther. 154, 339–345 (1966).

It is therefore a primary object to provide novel N-(substituted-4,5-dihydro-1H-pyrazol-4-yl)benzamides.

A further object is to provide N-(1-substituted-4,5-dihydro-1H-pyrazol-4-yl)benzamides having antiemetic and gastric-emptying enhancement properties.

A further object is to provide an efficient process for preparing N-(1-substituted-4,5-dihydro-1H-pyrazol-4-yl)benzamides.

An additional object is to provide novel compositions useful as anti-emetics and compositions for controlling gastric emptying.

DETAILED DESCRIPTION OF THE INVENTION

The compounds of this invention are prepared by oxidation of N-(1,2-disubstituted-4-pyrazolidinyl)benzamides. Various oxidizing agents such as oxygen, manganese dioxide and sodium metaperiodate can be used for the oxidation. The process of this invention for preparing compounds of Formula I is based on the discovery that sodium hypochlorite is an efficient oxidizer for the purpose. The equation for the oxidation is as follows:

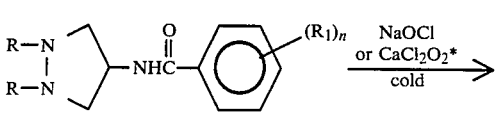

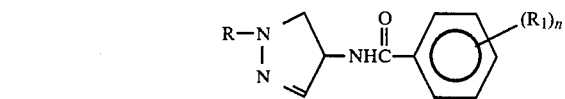

*(other alkali-metal or alkaline-earth hypochlorites may also be used)

wherein R=loweralkyl, phenylloweralkyl and cycloalkyl and $R^1$ and n are as defined under Formula I, or an acid addition salt thereof.

The oxidation is conducted in a polar protic solvent, any loweralkanol such as methanol, ethanol, propanol or isopropyl alcohol being suitable. The temperature should be at least as cold as 0° C. and not much below about −30° C. A temperature of −20° C. appears optimum and therefore it is preferred to conduct the reaction in the range of −10° to −30° C., most preferably about −20°. Sodium and calcium hypochlorite are the preferred oxidizing agents used in the reaction and may be added in the form of a dilute aqueous solution or a slurry. The product is suitably isolated by conventional means, illustratively by extracting with a suitable nonpolar solvent, column chromatographing and concentrating the eluant and washing the residue with a suitable solvent, recrystallizing if necessary.

Alternately, compounds of Formula I wherein $R_1$ is nitro may be catalytically reduced to give compounds wherein $R_1$ is —$NH_2$ or compounds wherein $R_1$ is a blocked amino group such as acetamido may be hydrolyzed under mildly acidic conditions to give compounds wherein $R_1$ is $-NH_2$.

Contemplated are compounds having the formula:

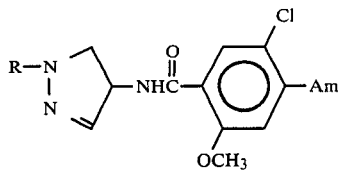

wherein R is loweralkyl and Am is selected from amino ($-NH_2$), methylamino or dimethylamino.

A preferred group of compounds encompassed by Formula I have the formula:

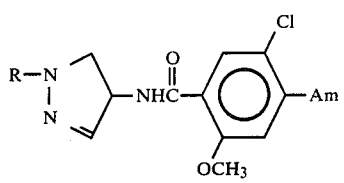

wherein R is loweralkyl and Am is selected from amino and methylamino. Consequently, it follows that compounds prepared by the process described above using hypochlorite oxidation are the compounds of Formula Ia.

The following examples are provided merely by way of illustrating the method of preparation and compounds and are not to be construed as limiting in nature.

EXAMPLE 1

4-Amino-5-chloro-N-(1-ethyl-4,5-dihydro-1H-pyrazol-4-yl)-2-methoxybenzamide

To a solution of 8.90 g (0.020 mole) of 4-amino-5-chloro-N-(1,2-diethyl-4-pyrazolidinyl)-2-methoxybenzamide succinate in 400 ml of reagent grade methanol, cooled to $-20°$ C. and under nitrogen atmosphere was added dropwise 80 ml of 5% aqueous sodium hypochlorite over a 20 min period while maintaining the reaction mixture at $-20°$ C. The reaction mixture was stirred for an additional one hour period at $0°$ C. then diluted with one liter of chloroform. The diluted mixture was washed with 500 ml of water. The aqueous layer was extracted with 200 ml of chloroform. The combined chloroform layers were dried over sodium sulfate and concentrated in vacuo. The crude product was partially purified by column chromatography on a silica column (eluted with ethyl acetate:hexane:methanol, 4.5:4.5:1). Further purification was effected by high pressure liquid chromatography, using the same solvent system as eluant. On evaporation, the residue was triturated with cold diethyl ether to give 1.90 g (32.0%) of title product, m.p. 132.5°–134.0° C.

Analysis: Calculated for $C_{13}H_{17}N_4O_2Cl$: C,52.61; H,5.78; N,18.87; Found: C,51.98; H,5.81; N,18.40.

EXAMPLE 2

4-Amino-5-chloro-N-(4,5-dihydro-1-methyl-1H-pyrazol-4-yl)-2-methoxybenzamide

To a solution of 1.44 g (0.00482 mole) of 4-amino-5-chloro-2-methoxy-N-(1,2-dimethyl-4-pyrazolidinyl)-benzamide in 100 ml of methanol, cooled to $-30°$ C. and under nitrogen atmosphere was added dropwise 10.5 ml (0.007 mole) of 5% aqueous sodium hypochlorite over a 15 minute period. The mixture was slowly warmed to $0°$ C. at which temperature it was stirred for 1 hr. The mixture was diluted with 250 ml of chloroform and extracted successively with 100 ml of water and 100 ml of saturated sodium chloride solution. The chloroform layer was dried over sodium sulfate and concentrated in vacuo. The concentrate was filtered through silica gel (eluted with ethyl acetate:hexane:methanol, 4.5:4.5:1). The filtrate was concentrated and the residue was triturated with cold diethyl ether to give 0.58 g (43%) of the title product as white powder, m.p. 173°–175° C.

Analysis: Calculated for $C_{12}H_{15}N_4O_2Cl$: C,50.97; H,5.35; N,19.82; Found: C,50.82; H,5.39; N,19.58.

EXAMPLE 3

N-(4,5-Dihydro-1-ethyl-1H-pyrazol-4-yl)4-fluorobenzamide

In accordance with the procedure of Example 2, N-(1,2-diethyl-4-pyrazolidinyl)-4-fluorobenzamide is reacted with sodium hypochlorite and the product is isolated.

EXAMPLE 4

N-(4,5-Dihydro-1-ethyl-1H-pyrazol-4-yl)-3,4,5-trimethoxybenzamide

In accordance with the procedure of Example 2, N-(1,2-dimethyl-4-pyrazolidinyl)-3,4,5-trimethoxybenzamide is reacted with sodium hypochlorite and the product is isolated.

EXAMPLE 5

N-(4,5-dihydro-1-ethyl-1H-pyrazol-4-yl)4-nitrobenzamide

In accordance with the procedure of Example 2, N-(1,2-diethyl-4-pyrazolidinyl)-4-nitrobenzamide is reacted with sodium hypochlorite and the product is isolated.

EXAMPLE 6

4-Amino-N-(4,5-dihydro-1-ethyl-1H-pyrazol-4-yl)benzamide

In accordance with the procedure of Example 2, 4-amino-N-(1,2-diethyl-4-pyrazolidinyl)benzamide is reacted with sodium hypochlorite and the product is isolated.

EXAMPLE 7

When in accordance with the procedure of Example 2 the following are reacted with sodium hypochlorite:
N-(1,2-dimethyl-4-pyrazolidinyl)-4-cyanobenzamide,
N-(1,2-dimethyl-4-pyrazolidinyl)-3-trifluorobenzamide,
N-(1,2-dimethyl-4-pyrazolidinyl-4-methylbenzamide,
N-(1,2-dimethyl-4-pyrazolidinyl-4-methoxybenzamide,
4-acetamido-N-(1,2-dimethyl-4-pyrazolidinyl)benzamide,
N-(1,2-dimethyl-4-pyrazolidinyl-2-methoxy-5-sulfamoylbenzamide, and
N-(1,2-dimethyl-4-pyrazolidinyl-4-hydroxybenzamide, there are obtained:
N-(4,5-dihydro-1-methyl-1H-pyrazol-4-yl)-4-cyanobenzamide,
N-(4,5-dihydro-1-methyl-1H-pyrazol-4-yl)-3-trifluoromethylbenzamide, N-(4,5-dihydro-1-methyl-1H-pyrazol-4-yl)-4-methylbenzamide, N-(4,5-dihydro-1-methyl-1H-pyrazol-4-yl)-4-methoxybenzamide, 4-acetamide-N-(4,5-dihydro-1-methyl-1H-pyrazol-4-yl)benzamide, N-(4,5-dihydro-1-methyl-1H-pyrazol-4-yl)-2-methoxy-5-sulfamoyl)benzamide, and N-(4,5-dihydro-1-methyl-1H-pyrazol-4-yl)-4-hydroxybenzamide.

EXAMPLE 8

N-(4,5-dihydro-1-ethyl-1H-pyrazol-4-yl)-4-(methylamino)-5-chloro-2-methoxybenzamide In accordance with the procedure of Example 2, 5-chloro-2-methoxy-4-(methylamino)-N-(1,2-diethyl-4-pyrazolidinyl)benzamide is reacted with sodium hypochlorite and the product is isolated.

EXAMPLE 9

N-(4,5-dihydro-1-ethyl-1H-pyrazol-4-yl)-5-chloro-4-(dimethylamino)-2-methoxybenzamide In accordance with the procedure of Example 2, 5-chloro-4-(dimethylamino)-2-methoxy-N-(1,2-diethyl-4-pyrazolidinyl)benzamide is reacted with sodium hypochlorite and the product is isolated.

PHARMACEUTICAL METHODS AND COMPOSITIONS

Generally, the method of controlling emesis and gastric emptying in accordance with this invention comprises administering internally to warm blooded animals, including human beings, certain N-(1-substituted-4,5-dihydro-1H-pyrazol-4-yl)benzamides of Formula I, preferably Formula Ia, in a wide variety of pharmaceutical forms well known in the art, preferably with a non-toxic pharmaceutical carrier such as is described below in an amount to control emesis and/or facilitate gastric emptying. The active agent is administered orally, subcutaneously, intravenously or intramuscularly, or parenterally and, if necessary, in repeated doses until satisfactory response is obtained. The daily dosage is from about 20 to about 300 mg of active medication, advantageously from about 10 mg to 50 mg.

The pharmaceutical compositions for general use as anti-emetics and gastric emptiers of this invention comprise at least one of the compositions of Formula I, preferably Formula Ia above, as active ingredients in an amount to provide effective anti-emetic or gastric emptying action. The compositions contain 5.0 to 100 mg active medicament per unit dose. Preferably, the compositions contain from about 10 mg to 100 mg of medicament, advantageously from about 10 mg to about 50 mg per unit dose. The compounds are thus presented in a therapeutic composition suitable for oral, parenteral, subcutaneous, intramuscular, intraperitoneal or intravenous administration. Thus, for example, compositions for oral administration can take the form of elixirs, capsules, tablets or coated tablets containing carriers conveniently used in the pharmaceutical art. Exemplary of solid carriers and including tableting and capsulating excipients are lactose, sucrose, potato and maize starches, talc, gelatin, agar, pectin or acacia, stearic and silicic acids, magnesium, stearate, terra alba and polyvinyl pyrrolidone.

For parenteral administration, the carrier or excipient can be comprised of a sterile parenterally acceptable liquid; e.g., water or arachis oil contained in ampoules.

In all of the above, it is only necessary that a suitable effective dosage will be consistent with the dosage form employed. The exact individual dosages, as well as daily dosages, will of course be determined according to standard medical principles under the direction of a physician or veterinarian. Generally, the pharmacology tests on rats in comparison to metoclopramide suggests slightly more active agent selected from a compound of Formula Ia would be required for a given anti-emetic effect or gastric emptying effect than would be required for metoclopramide and dosages can thereby be estimated to some extent.

The principles, preferred embodiments and modes of operation of the present invention have been described in the foregoing specification. The invention which is intended to be protected herein, however, is not to be construed as limited to the particular forms disclosed, since these ae to be regarded as illustrative rather than restrictive. Variations and changes may be made by those skilled in the art without departing from the spirit of the invention and it is therefore understood that the invention is to be limited only by the scope of the appended claims.

What is claimed is:

1. A compound selected from the group consisting of N-(1-substituted-4,5-dihydro-1H-pyrazol-4-yl)benzamides having the formula:

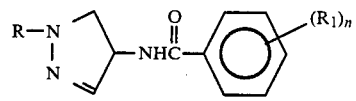

wherein;
R is selected from loweralkyl, cycloalkyl or phenyl-loweralkyl;
$R_1$ is selected from hydroxy, cyano, nitro, amino, methylamino, dimethylamino, halo, trifluoromethyl, loweralkyl, loweralkoxy, sulfamoyl, or acetamido;
n is an integer from 1 to 3 inclusive, and
$R_1$ can be the same radical or different radicals.

2. The compound of claim 1 which is 4-amino-5-chloro-N-(1-ethyl-4,5-dihydro-1H-pyrazol-4-yl)-2-methoxybenzamide.

3. The compound of claim 1 which is 4-amino-5-chloro-N-(4,5-dihydro-1-methyl-1H-pyrazol-4-yl)-2-methoxybenzamide.

4. A compound selected from the group consisting of N-(1-substituted-4,5-dihydro-1H-pyrazol-4-yl)benzamides having the formula:

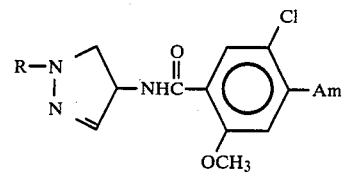

wherein R is loweralkyl and Am is selected from amino (—NH₂), methylamino or dimethylamino.

5. A method for treating warm blooded animals for emesis which comprises internally administering thereto an emesis-inhibiting effective amount of a compound selected from the group consisting of N-(1-substituted-4,5-dihydro-1H-pyrazol-4-yl)benzamides having the formula:

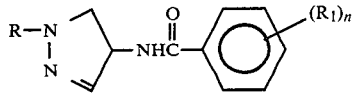

wherein:
R is selected from loweralkyl, cycloalkyl or phenyl-loweralkyl;
$R_1$ is selected from hydroxy, cyano, nitro, amino, methylamino, dimethylamino, halo, trifluoromethyl, loweralkyl, loweralkoxy, sulfamoyl or acetamido,
n is an integer from 1 to 3 inclusive, and
$R_1$ can be the same or different.

6. The method of claim 5 wherein the compound is 4-amino-5-chloro-N-(1-ethyl-4,5-dihydro-1H-pyrazol-4-yl)-2-methoxybenzamide.

7. The method of claim 5 wherein the compound is 4-amino-5-chloro-N-(4,5-dihydro-1-methyl-1H-pyrazol-4-yl)-2-methoxybenzamide.

8. A pharmaceutical composition useful for its antiemetic and gastric emptying properties comprising (a) an emetic inhibiting and gastric emptying effective amount of a compound selected from the group consisting of N-(1-substituted-4,5-dihydro-1H-pyrazol-4-yl)benzamides having the formula:

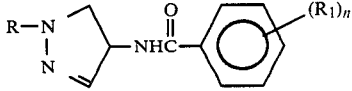

wherein;
R is selected from loweralkyl, cycloalkyl or phenyl-loweralkyl;
$R_1$ is selected from hydroxy, cyano, nitro, amino, methylamino, dimethylamino, halo, trifluoromethyl, lower-alkyl, loweralkoxy, sulfamoyl, or acetamido,
n is an integer from 1 to 3, and
$R_1$ can be the same or different, and
(b) a pharmaceutically acceptable carrier therefor.

9. The composition of claim 8 wherein the compound is 4-amino-5-chloro-N-(1-ethyl-4,5-dihydro-1H-pyrazol-4-yl)-2-methoxybenzamide.

10. The composition of claim 8 wherein the compound is 4-amino-5-chloro-N-(4,5-dihydro-1-methyl-1H-pyrazol-4-yl)-2-methoxybenzamide.

* * * * *